US006398817B1

United States Patent
Hellberg et al.

(10) Patent No.: US 6,398,817 B1
(45) Date of Patent: Jun. 4, 2002

(54) LOCKING DEVICE FOR A PROTHESIS

(75) Inventors: Kenneth Hellberg, Vallentuna; Jan Johansson, Kungsangen, both of (SE)

(73) Assignee: Centri AB, Jarfalla (SE)

( * ) Notice: Subject to any disclaimer, the term of this patent is extended or adjusted under 35 U.S.C. 154(b) by 0 days.

(21) Appl. No.: 09/532,016

(22) Filed: Mar. 21, 2000

Related U.S. Application Data

(63) Continuation of application No. PCT/SE98/01711, filed on Sep. 23, 1998.

(30) Foreign Application Priority Data

Sep. 26, 1997 (SE) .............................................. 9703487

(51) Int. Cl.$^7$ ................................................ A61F 2/62
(52) U.S. Cl. ........................................ 623/38; 623/33
(58) Field of Search ................................ 623/38, 32–37

(56) References Cited

U.S. PATENT DOCUMENTS

| 1,302,336 A | * | 4/1919 | Erickson ...................... 623/38 |
| 3,597,767 A | | 8/1971 | Prahl |
| 5,047,063 A | | 9/1991 | Chen |

FOREIGN PATENT DOCUMENTS

| CH | 638 095 | * | 9/1983 | .................. 623/38 |
| EP | 0 187 516 | | 7/1986 | |
| FR | 2 410 998 | | 7/1979 | |
| GB | 2 274 398 | * | 7/1994 | .................. 623/38 |
| JP | 8-89519 | * | 4/1996 | .................. 623/38 |
| WO | WO 93/17640 | | 9/1993 | |

* cited by examiner

Primary Examiner—David H. Willse
(74) Attorney, Agent, or Firm—Young & Thompson

(57) ABSTRACT

A novel way of locking and unlocking an adjustment device for an artificial leg or arm makes it possible to perform an adjustment of the prosthesis, without necessitating disassembly of the prosthesis or the removal of the prosthesis from the patient. This facilitates the work in adjusting the translatory position and the angular position, and the adjustment device also offers a further degree of freedom by the addition of the possibility of distal adjustment. The novel combination provides a locking ring (40) on the adjustment head. The locking ring offers a stable, adjustable locking of the adjustment head against a coupling sleeve (50) on the stump, while at the same time fixing the translatory position of the prosthesis. The prosthesis is then provided with a stable, adjustable setting of the distal length of the prosthesis by means of the locking ring (40), which greatly facilitates fine adjustment of the length of the prosthesis, since there is no need to disassemble the prosthesis for performing such a distal length adjustment. The angular adjustment is carried out by means of a pyramid adapter pin (23) which is arranged either in the upper, or in the lower part of the adjustment head. Inclined adjustment screws corresponding to the inclined sides of the pyramid adapter pin are arranged in the corresponding upper or lower part of the adjustment head. The arrangement allows a simple way of disassembling the adjustment head in two parts.

10 Claims, 4 Drawing Sheets

LOCKING DEVICE FOR A PROTHESIS

Figure 1:
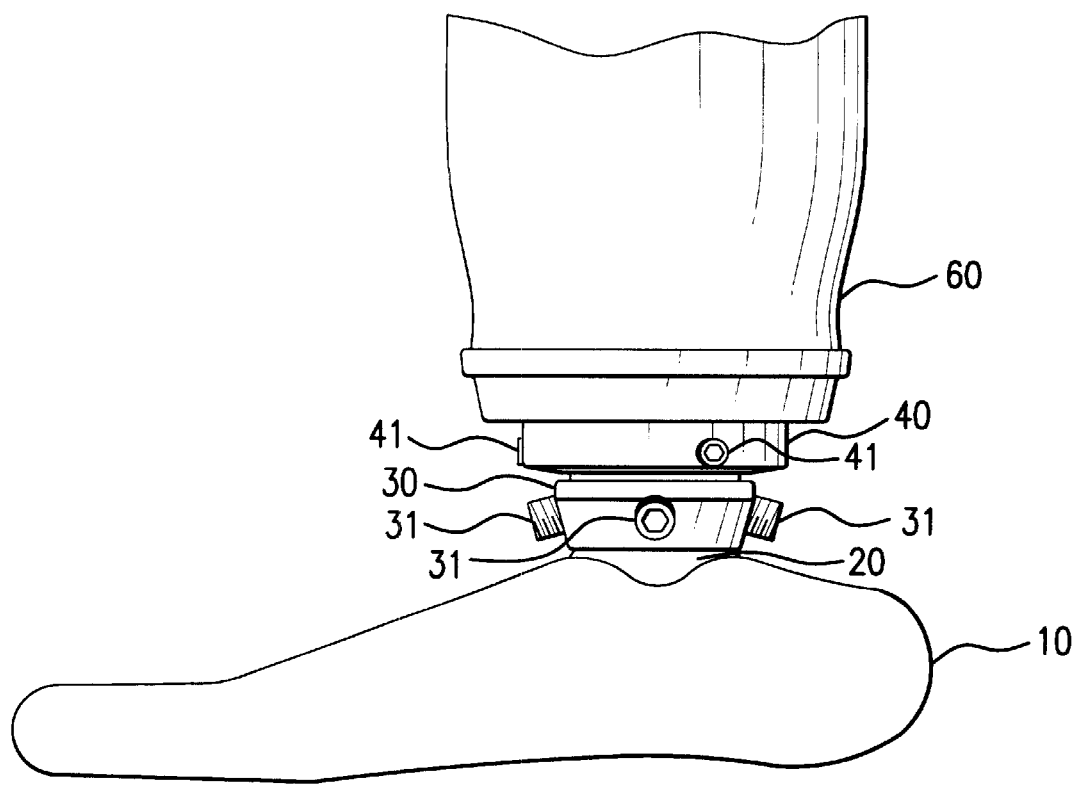

This application is a continuation of international application PCT/SE98/01711 filed Sep. 23, 1998, which designated the United States.

TECHNICAL FIELD

The present invention relates to a device for a prosthesis, and more specifically, a novel combination is shown, with a novel way of locking and opening an adjustment device for an artificial arm or leg.

PRIOR ART

On the market, there is available, a number of different solutions for artificial legs, for example. A such device is generally comprised of a tubular member which at its upper end is attached to a sleeve which is adapted to receive the stump of the leg, and it is further, by means of a second joint coupling fixed to a foot prosthesis or a corresponding device or member. It is important that the tubular member, when being attached to the stump, can be adjusted in both the angular and translatory direction, so that the user does not apply load in an unnatural way to the prosthesis and the stump, which would result in the pattern of motion of the prosthetic device becoming unnatural when the patient moves, and in that the knee joint and the muscles of the upper part of the leg may be loaded in an unnatural way.

The Swedish patent no. SE 454 046 shows such a device which, by means of an adjustment head 11 arranged at the upper end 4 of the tubular member 10, having a first member 16, allows setting of the angular position of the tubular member relative to an imagined load line. Moreover, other members 12, 13 allow a translatory displacement of the tubular member 10 relative to the adjustment head 11. The adjustment members 16 and 12, 13 respectively, allow a basic adjustment of the tubular member, once the prosthesis has been fitted.

Another Swedish patent, no. 360 257 of 1970, shows an adjustable coupling between two elements in an arm or leg prosthesis, or the like. Said device has a four-sided stud, having the shape of a truncated pyramid with four sides, divergently extending from the base. The device only allows angular adjustment in two defined planes in relation to the socket, but no translatory adjustment of the type disclosed in the Swedish patent SE 454 046 is provided for.

None of the prior art devices provide a prosthetic device which, without unnecessary disassembly or removal of the prosthesis, provides for a easy angular adjustment in all planes in relation to an imagined load line, and at the same time a translatory adjustment. Further, such systems do not normally combine easiness of disassembly, and an acceptable mechanical strength.

None of the known devices does, either, provide the possibility for a simple distal adjustment. The reasons necessitating such a length adjustment may be that the patient during the first trial is unwilling to fully load to the prosthesis, which makes it difficult to find the right length from the start. It is usually possible to see if the length of the prosthesis is wrong, only after the user of the prosthesis has gotten used to the prosthesis, and it would then be desirable to be able to make a fine adjustment of the length of the prosthesis. The adjustments in question are, then, often small adjustments in relation to the total length of the prosthesis, but these millimeters are important for the user of the prosthesis, in order to achieve a complete functional ability.

SHORT DESCRIPTION OF THE INVENTION

The present invention thus relates to a novel combination, with a novel way of locking and opening an adjustment device for a prosthesis. Said novel combination makes it easy to perform an adjustment of a prosthesis without the need to disassemble the prosthesis system, or the user having to remove the prosthesis. This facilitates the adjustment of a prosthesis in an important way, and it also provides another degree of freedom, by the addition of the possibility of distal adjustment.

In accordance with the present invention there is provided a locking ring for achieving a stable adjustable locking of the adjustment head against a coupling sleeve on the stump, also locking the translatory position of the prosthesis, which in an important way facilitates the translatory positioning of a leg prosthesis, since said prosthesis need not be disassembled or removed from the patient.

Thus, the present invention provides, by means of said locking ring, a stable and adjustable setting of the distal length of the prosthesis, which greatly facilitates adjustment of the length of the prosthesis, since it is no longer required that the prosthesis be disassembled or removed by the patient, in order to perform for such a fine adjustment of the length.

The object of the present invention is setting of the translatory position and distal length of the prosthesis by means of first adjustment means, and then an easy locking of the system in said position by means of the novel locking function. The upper part of the first adjustment means is resting against an upper coupling sleeve, which is fixed to the prosthesis sleeve. Said coupling sleeve has a central hole which allows the translatory displacement of a screw extending therethrough, in relation to the upper coupling sleeve. Said coupling sleeve also has a lower plane surface, against which the upper plane surface of the upper part of the adjustment head is abutting.

The upper part of the adjustment head comprises a first part of angular adjustment means, into a through hole into which the screw is screwed, and further it comprises the locking ring. The upper plane surface of the locking ring abuts against the plane surface of the coupling sleeve, and the position of the locking ring in relation to the upper part of the means for angular adjustment then determines the distal length of the prosthetic device. The adjustment head is further translatory adjustable in all directions in the plane of the coupling sleeve, and is locked in a stable way by means of the upper plane surface of the locking ring, the force of which is resisted by the central screw.

Additional adjustment means are used for the angular adjustment. Said additional adjustment means comprise an angular member, having a distal convex surface and a plurality of threaded holes inclining slightly upwards, into which adjustment screws, preferably of the socket head cap screw type, are used for providing the angular setting. At least three adjustment screws are required for achieving a stable angular setting, and for practical reasons, there should be no more than five screws. The adjustment screws are then screwed against a second part of the angular adjustment means for achieving an angular adjustment. The angular adjustment means (FIG. 2 and FIG. 3) may be comprised of, one the one hand, a pyramid adapter, which in turn is comprised of a pyramid adapter stud, and a convex outer surface arranged around said stud, which is attached, in a manner which is known to the artisan, e.g. to a an artificial foot, an artificial knee joint or a tubular prosthesis member. The pyramid adapter has a number of planes which correspond to the number of adjustment screws, said planes having an inclination such, that they lie mainly at right angles in relation to the adjustment screws. Further, the adjustment head is provided with a sleeve member having a concave surface, which rests against a convex surface around the pyramid adapter pin, thus taking up the axial load on the adjustment element, while the locking screws lock the angular position.

The angular means may on the other hand, in a second embodiment, be comprised of a tubular sleeve member which, in turn, has an inner, spherical surface which is attached to a support plate, the plane side of which essentially corresponds to the inclination of the end of a second screw member, which is screwed through the flange of the tubular sleeve member.

SHORT DESCRIPTION OF THE DRAWINGS

Figure 2:
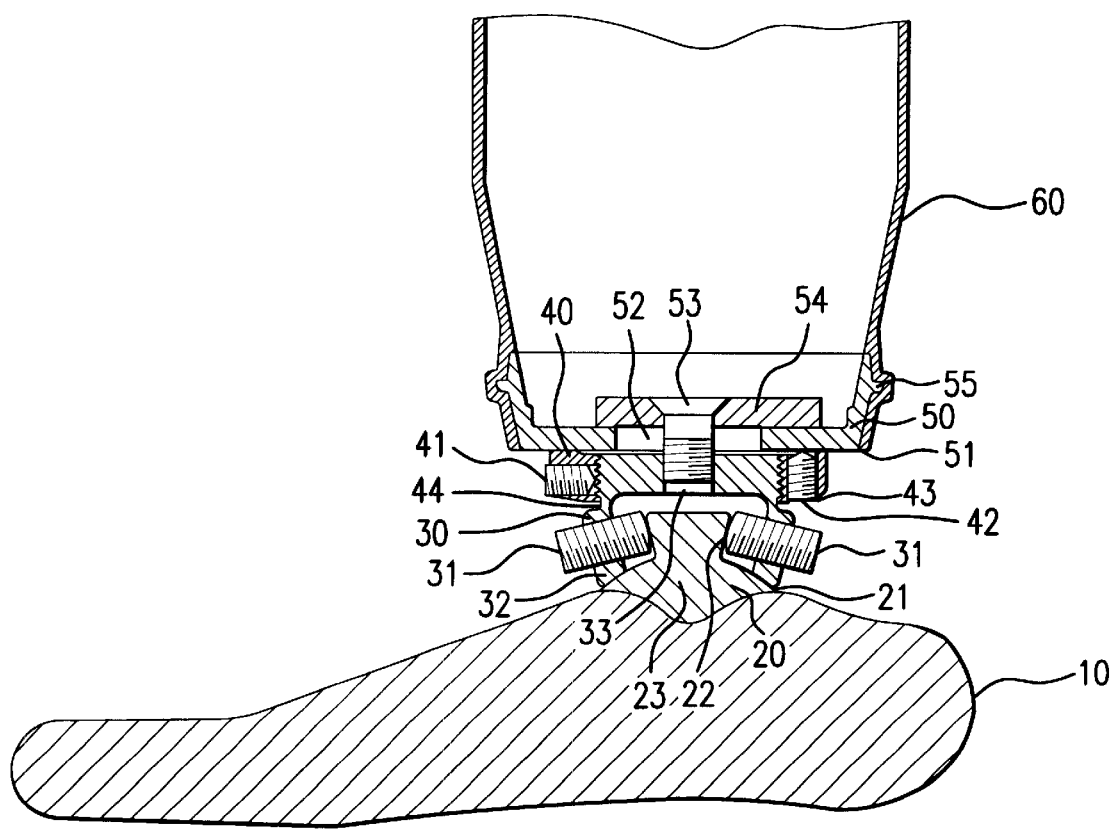
Figure 3:
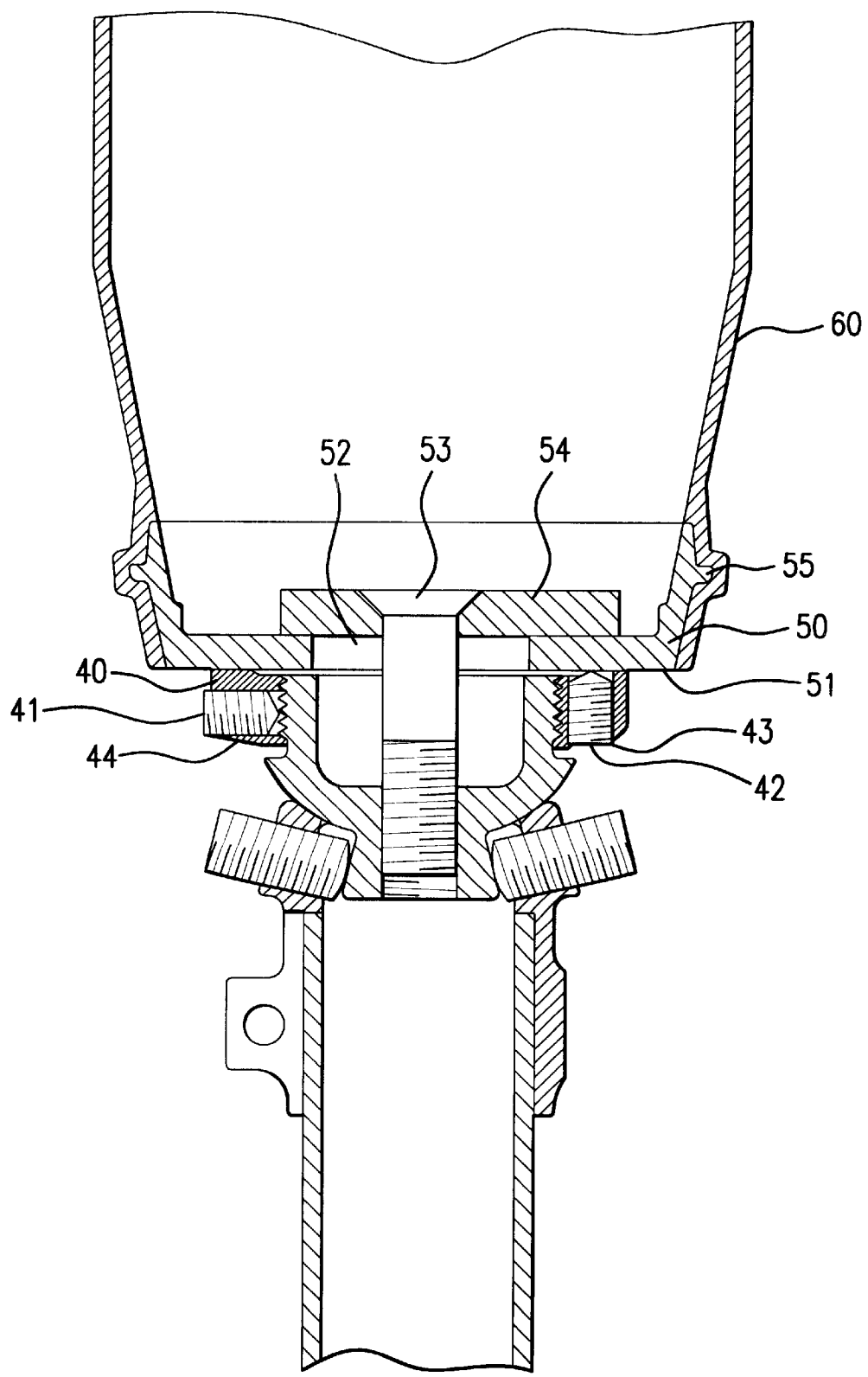
Figure 4:
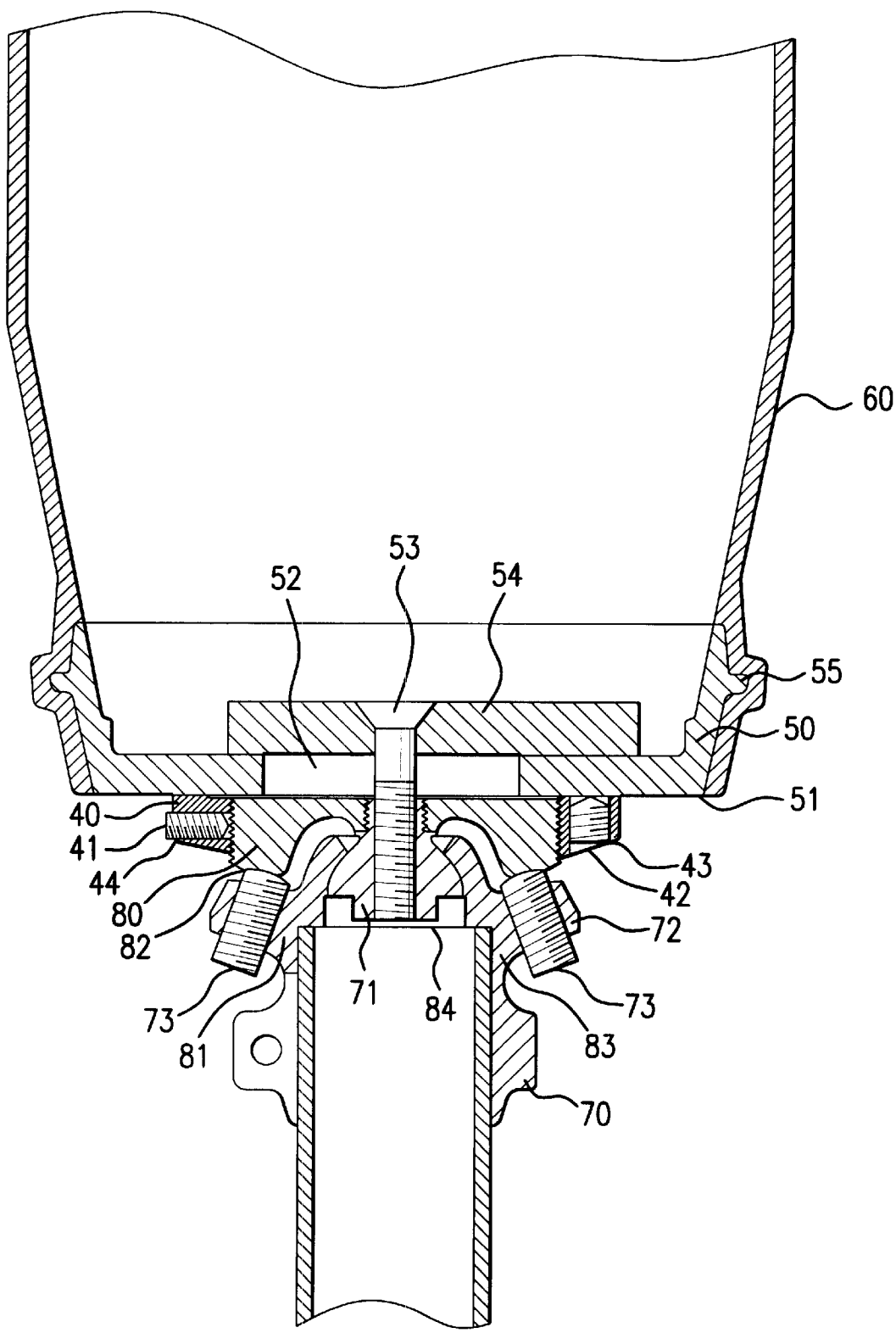

The invention will now be described in a preferred, illustrative embodiment, reference being made to the appended drawings, where the same reference signs refer to identical, or corresponding elements, and in which FIG. 1 shows an illustrative embodiment of a prosthetic device according to the present invention, FIG. 2 shows a longitudinal view, in section, of the embodiment in FIG. 1, FIG. 3 shows the invention, provided with a second embodiment of the angular adjustment of the prosthesis, and FIG. 4 shows the invention with yet another possible arrangement for angular adjustment.

DESCRIPTION OF ILLUSTRATIVE EMBODIMENTS

FIG. 1 shows an illustrative embodiment of a part of a prosthesis in accordance with the present invention, while FIG. 2 shows a view in section of the device according to FIG. 1. The prosthesis has as its main component, in a way which is known to the artisan, an artificial foot 10, an adjustment head and a prosthesis sleeve.

The artificial foot 10 is in a conventional way attached to a proximal pyramid adapter 20, which will then constitute a lower part of the adjustment head. In the illustrative embodiment, the pyramid adapter has a convex surface surrounding a pyramid adapter stud which, in the illuminating embodiment, has four inwardly inclined surfaces. However, the pyramid adapter stud may, in another embodiment, have three or five inclined surfaces, which then co-operate with an equal number of adjustment screws 31 in the distal end of the adjustment head 30.

Thus, in the illustrative embodiment, one part of the angular adjustment means is formed by the pyramid adapter 20 which, at the distal end is attached to an artificial foot 10, but it can equally well be attached to a tubular member, or a knee joint, or be turned in the opposite direction, then being arranged on that part of the adjustment head which is adjacent to prosthesis sleeve 60.

In the illustrative embodiment according to FIG. 3, the angular adjustment means are comprised of said pyramid adapter, but it could also, in accordance with FIG. 4 be comprised of an outer tubular sleeve member 70, having an inner spherical surface, bearing against a second spherical surface 81. By means of four further adjustment screws 73, threaded through the flange 72 of the sleeve against an inclined plane 82, the inclination of which approximately corresponds to angle of the angular adjustment screw 73 in relation to the centre line of the angular adjustment means, the inclination of the tubular sleeve member is set. The tubular sleeve member could, instead of four inclined angular adjustment screws 73, be provided with three or five inclined screws 73. Accordingly, the screws 73 lock the angle against that part of the adjustment head 80 which has a spherical element 83. The spherical element 83 is attached to the part 80 of the adjustment head by means of an internal or external mutual threading, and also by means of the screw 53, which is screwed into the spherical element 80.

The drawback of the embodiment according to FIG. 4 is, that the adjustment head is not as easy to disassemble, as in the case with the pyramid adapter stud.

The inclining sides 22 of the pyramid adapter stud 23 essentially correspond to the inclination of the adjustment screws 31 inside the angular member 30 such, that the adjustment screws will abut against the inclining sides 22 of the pyramid adapter stud at approximately right angles. The adjustment head is thus provided with a plurality of radially arranged adjustment screws 31, preferably of the socket head cap screw type. The direction of the adjustment screws is slightly inclined in relation to the centre line of the adjustment head, in order to abut against the corresponding number of plane surfaces 22 of the pyramid adapter stud 23.

The adjustment head, comprising the sleeve element 30 is further comprised of a distal, concave surface 32, which co-operates with a corresponding convex surface 21 at the pyramid adapter 20. Said convex surface 21 is adapted to abut against the concave surface 32 of the upper sleeve. The locking ring 40 is threaded onto the part 30 of the adjustment head, and has a plane surface on the side adjacent to the prosthesis sleeve 60, said plane surface abutting against a lower plane surface on an upper coupling sleeve 50 which is attached to the prosthetic sleeve 60, e.g. by moulding. The locking ring 40 with the element 30, together with the upper coupling sleeve 50 thus comprise the upper portion of the entire adjustment head.

The coupling sleeve 50 has a flange 55 onto which the prosthetic sleeve 60 is moulded. The coupling sleeve 50 further has, in its lower plane surface, a through hole 52, the diameter of which is much larger than the diameter of a bolt or a screw 53 which is threaded into a through hole 33 in the upper part 30 of the adjustment head. Said screw 33 is further, in the illuminating embodiment, countersunk in an upper washer 54 which regardless of the position of the screw 53 inside the through hole, essentially covers the hole 52. The upper coupling sleeve 50, the washer 54, the screw, 53, the locking ring 40 and the part 30 of the adjustment head thus constitute the length adjustment of the prosthesis and adjustment in the translatory direction, while the part 30 of the adjustment head with its concave surface 32 and the screws 31, together with the proximal pyramid adapter 20 with its inclining planes 22 and the convex surface 21 constitute the device for the angular adjustment of the artificial foot 10.

In this embodiment there is further provided, in the locking ring 40, a plurality of radial holes which are used for receiving a tool, by means of which the locking ring is more easily turned, and thus locking or unlocking the translatory movement without having to disassemble the prosthesis. Further, a number of said holes are threaded, for the purpose of locking the locking ring 40 against the part 30 of the adjustment head by means of a locking screw 41, which is arranged in a radial, threaded hole in the locking ring 40 against the part 30, which provides additional locking between the locking ring 40 and the adjustment head. Further, in order to achieve a secure locking against the coupling sleeve 50, the locking ring 40 is provided with a plurality of axial threaded holes 43. Into the holes 43 are inserted locking screws 42 which, by means of a pointed end engage the plane surface 51 of the coupling sleeve 50, for additional mutual locking of the locking ring and the angular adjustment means to the coupling sleeve in the set translatory position.

By means of the structure according to the present invention, a combination of a device for distal length adjustment, translatory adjustment device and a device for angular adjustment is obtained. In accordance with the present invention, it is possible to obtain the advantage, over for example the known structure of the Swedish patent SE 454 046, of the adjustment head being easy to disassemble, the distal portion being removable from the foot with the pyramid adapter stud, without the need to remove the prosthetic sleeve 60 from the stump. Further, the locking ring 40 offers the possibility of locking and unlocking the translatory setting without requiring that the prosthesis be disassembled or removed from the stump, which facilitates the setting of the prosthesis to a great extent. Further, the locking by means of the locking ring 40 offers the possibility of adjusting the distal length of the prosthesis without having to disassemble the prosthesis as such.

The prosthetic device according to the present invention may be subjected to modifications and may be changed in a number of ways by the artisan, without departing from the spirit and scope of the invention, which are apparent from the appended patent claims.

What is claimed is:

1. A locking device for attachment of an artificial limb to an amputee's leg, comprising a coupling member arranged in a distal end of a sleeve that is adapted to receive the stump of the leg, and an adjustment head arranged on the artificial limb and connectable to the coupling member in laterally displaced positions relative thereto, wherein a locking ring is carried externally about the adjustment head, said locking ring being axially displaceable on the adjustment head and effective for adjustment of a distal length of the artificial limb, and effective for fixation of said adjusted distal length by frictionally arresting the locking ring on the adjustment head with an upper end of the locking ring in abutting contact with a lower surface of the coupling member, whereby the ring simultaneously effects a fixation of a translatory position of the artificial limb relative to the coupling member through the abutting contact with said lower surface of the coupling member.

2. The locking device of claim 1, wherein the adjustment head comprises a first portion connectable to the coupling member in the distal end of the sleeve, the first portion being pivotally connected with a second portion arranged on the artificial limb, said first portion of the adjustment head carrying the locking ring in abutting contact with the lower surface of the coupling member for setting the translatory position of the artificial limb, and said second portion carrying set screws engaging the first portion for setting an angular position of the artificial limb, relative to the coupling member.

3. The locking device of claim 2, wherein the first portion of the adjustment head extends through a central opening of the coupling member by means of a screw in threaded engagement with said first portion, the free end of said screw engaging a washer element substantially covering said opening, the opening having a diameter that exceeds the diameter of the screw for translatory displacement of the first portion of the adjustment head relative to the coupling member, and the coupling member being clamped between the washer element and the locking ring when the locking ring is frictionally arrested on the first portion in abutting contact with the lower surface of the coupling member.

4. The locking device of claim 3, wherein the locking ring is carried in threaded engagement externally about the adjustment head and carrying one or more radial set screws for rotationally arresting the locking ring by the set screws engaging the threaded exterior of the adjustment head, and also carrying one or more axial set screws for engagement with the lower surface of the coupling member and thus for further securing the translatory position of the adjustment head relative to the coupling member.

5. The locking device of claim 2, wherein a convex surface formed on the first portion of the adjustment head is pivotally supported on a concave surface formed on the second portion of the adjustment head, said first portion being connected with said second portion by means of a pyramid shaped stud with inclined surfaces carried by the first portion and being received in the second portion such that each said inclined surface is engaged by a corresponding set screw carried by the second portion of the adjustment head for setting the relative angular position of the first and second portions of the adjustment head.

6. The locking device of claim 5, wherein the locking ring is carried in threaded engagement externally about the adjustment head and carrying one or more radial set screws for rotationally arresting the locking ring by the set screws engaging the threaded exterior of the adjustment head, and also carrying one or more axial set screws for engagement with the lower surface of the coupling member and thus for further securing the translatory position of the adjustment head relative to the coupling member.

7. The locking device of claim 2, wherein a convex surface connectable to the first portion of the adjustment head is pivotally supported on a concave surface formed on the second portion of the adjustment head, said convex surface being received within said concave surface for connecting said first portion with said second portion of the adjustment head, and set screws carried on said second portion engaging said first portion for setting the relative angular position of the first and second portions of the adjustment head.

8. The locking device of claim 7, wherein the locking ring is carried in threaded engagement externally about the adjustment head and carrying one or more radial set screws for rotationally arresting the locking ring by the set screws engaging the threaded exterior of the adjustment head, and also carrying one or more axial set screws for engagement with the lower surface of the coupling member and thus for further securing the translatory position of the adjustment head relative to the coupling member.

9. The locking device of claim 2, wherein the locking ring is carried in threaded engagement externally about the adjustment head and carrying one or more radial set screws for rotationally arresting the locking ring by the set screws engaging the threaded exterior of the adjustment head, and also carrying one or more axial set screws for engagement with the lower surface of the coupling member and thus for further securing the translatory position of the adjustment head relative to the coupling member.

10. The locking device of claim 1, wherein the locking ring is carried in threaded engagement externally about the adjustment head and carrying one or more radial set screws for rotationally arresting the locking ring by the set screws engaging the threaded exterior of the adjustment head, and also carrying one or more axial set screws for engagement with the lower surface of the coupling member and thus for further securing the translatory position of the adjustment head relative to the coupling member.

* * * * *